United States Patent
Arslanouk

(10) Patent No.: US 10,111,505 B2
(45) Date of Patent: Oct. 30, 2018

(54) AEROSOL COMPOSITION FOR THE PREVENTION OF SYMPTOMS OF METAL INDUCED ALLERGY AND A METHOD OF SYNTHESIZING THE SAME

(71) Applicant: Tatiana Tara Arslanouk, Wayne, NJ (US)

(72) Inventor: Tatiana Tara Arslanouk, Wayne, NJ (US)

( * ) Notice: Subject to any disclaimer, the term of this patent is extended or adjusted under 35 U.S.C. 154(b) by 0 days.

(21) Appl. No.: 15/654,013

(22) Filed: Jul. 19, 2017

(65) Prior Publication Data

US 2017/0311687 A1    Nov. 2, 2017

(51) Int. Cl.
*A61K 31/075*   (2006.01)
*A44C 27/00*    (2006.01)

(52) U.S. Cl.
CPC .......... *A44C 27/007* (2013.01); *A61K 31/075* (2013.01); *A61K 2800/526* (2013.01)

(58) Field of Classification Search
CPC combination set(s) only.
See application file for complete search history.

(56) References Cited

U.S. PATENT DOCUMENTS

| | | | | |
|---|---|---|---|---|
| 5,716,603 A | * | 2/1998 | Chen | A61K 8/87 424/61 |
| 2009/0053159 A1 | * | 2/2009 | Brun | A61K 8/26 424/70.12 |
| 2012/0100089 A1 | * | 4/2012 | Barba | A61K 8/06 424/63 |
| 2012/0322870 A1 | * | 12/2012 | Matsuo | A01N 53/00 514/521 |

* cited by examiner

*Primary Examiner* — Kara B Boyle
(74) *Attorney, Agent, or Firm* — Barry Choobin; Patent 360

(57) ABSTRACT

The embodiments herein disclose hypoallergenic, metal surface sealant clear aerosol composition to be used on metals (specifically jewelry) to prevent skin allergies and the process of tarnishing of metal. The method of synthesizing hypoallergenic metal surface sealant clear aerosol composition comprises the following steps. The paraloid-B-48 material (10.59 wt %) is added to ethyl acetate (31.77 wt %) slowly under constant agitation. The mixture comprising paraloid-B-48 material and ethyl acetate is agitated till no lumps are present. The butyl acetate (8.47 wt %), TAXIB Plasticizer (0.70 wt %), propylene glycol monomethyl ether (PM) acetate (19.77 wt %), ethyl acetate (28.24 wt %), Chemia #46210 Lavandin (0.42 wt %) and dimethyl ether to the mixture comprising paraloid-B-48 material and ethyl acetate are added to the mixture comprising paraloid B-48 material and ethyl acetate to obtain a composition. The composition is blended at a predetermined speed to uniformly mix the components.

8 Claims, 1 Drawing Sheet

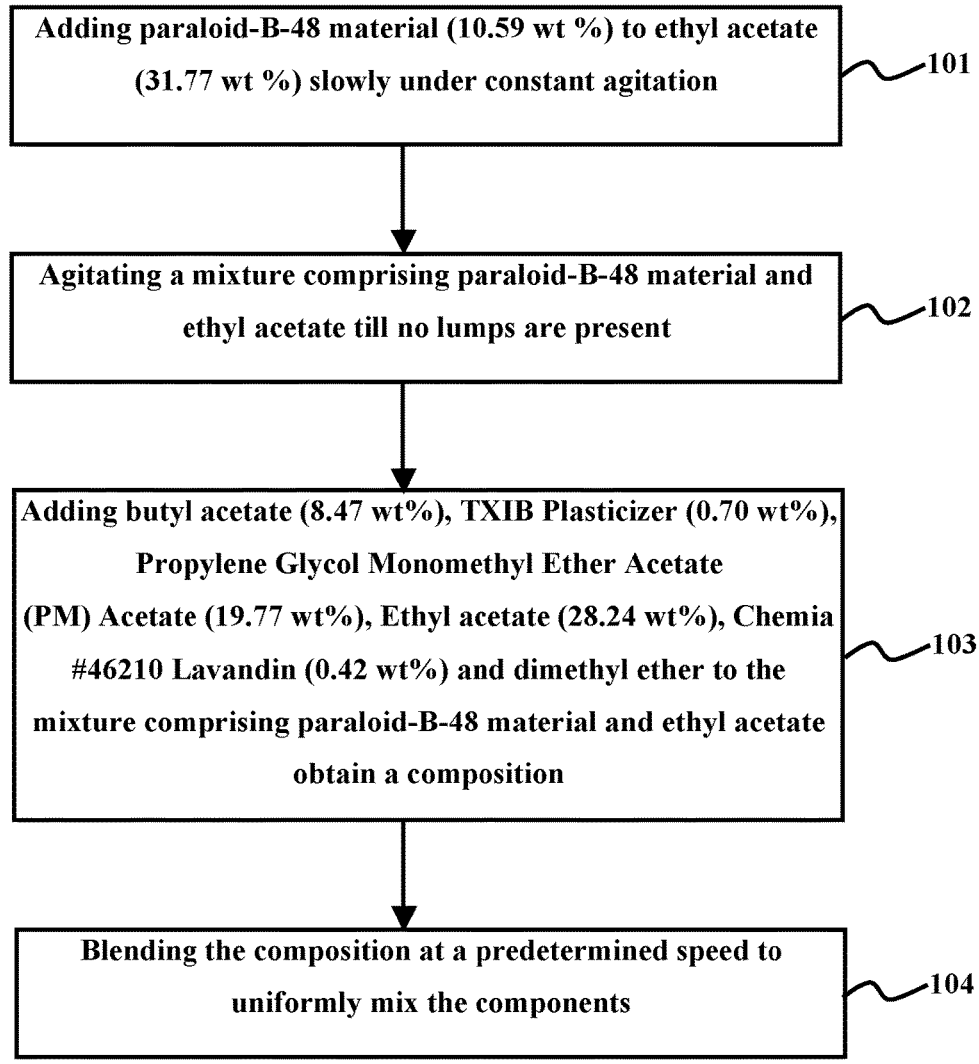

AEROSOL COMPOSITION FOR THE PREVENTION OF SYMPTOMS OF METAL INDUCED ALLERGY AND A METHOD OF SYNTHESIZING THE SAME

BACKGROUND

Technical Field

The embodiments herein are generally related to a field of aerosols. The embodiments herein are particularly related to a composition for application on the metal surface for preventing symptoms of metal induced allergic contact dermatitis. The embodiments herein are more particularly related to hypoallergenic metal sealant aerosol composition to prevent skin allergies and avoid tarnishing of metal surface.

Description of the Related Art

Allergy or allergic reaction is a condition caused by hypersensitivity of the immune system against some factors in the environment which usually causes little or no problem in most people. The common allergic disease includes hay fever, food allergy, atopic dermatitis and anaphylaxis. The common allergy causing agents are pollen, food items, metals, dust particles and insect stings.

Fashion Jewelry (also known as costume jewelry) is extremely cost-effective because of the base metals used to craft them. Unfortunately, its negative tendencies, such as rapid tarnishing, skin discoloration, irritation and/or allergies, causes a reluctance in buyers. As a result, a majority of consumers avoid base-metal alloys entirely.

"Base Metals" are metals that oxidize, tarnish or corrode relatively easily when exposed to air, moisture, humidity and skin oils/acids. Base metals are widely used in commercial and industrial applications. They are more abundant in nature and therefore far cheaper than precious metals such as gold, silver and platinum. The very common example of base metal is nickel.

Some manufacturers define "Nickel-Free" as free of nickel in the plating or overlay but utilize nickel alloys in the base metal to increase durability and reduce the cost of goods. When the plating or overlay wears, even microscopically, an allergic reaction to the nickel in the base metal can occur.

Allergic contact dermatitis (ACD) is a form of contact dermatitis which is a manifestation of an allergic response caused by contact with a substance. The other type of the ACD is irritant contact dermatitis (ICD).

The causative agents of the allergic contact dermatitis (ACD) is nickel (significant cause of allergy, found mainly in artificial jewelry, clasps, buttons), gold sodium thiosulfate (precious metal found in jewelry or dental implants), chromium, thiomersal (mercury compound), cobalt chloride (found in metal plated objects such as snaps, buttons and tools) etc.

Nickel is the main cause of allergic contact dermatitis (ACD) in many individuals. The ADC manifestations initially occurs in those skin regions in direct contact with commonly used metal accessories, such as earrings, buttons, zippers, bracelets, necklaces, coins, buckles, watches, keys, cell phones, eyeglass frames, jewelry for body piercing and cooking utensils. The silver alloy, white gold, 14 carat yellow gold and platinum may contain nickel in variable percentages depending on alloy purity. Furthermore, nickel is present in several objects subjected to chromium plating. Nickel is also present in a plurality of alloys which are used for fabricating appliances, desks, tools and machinery, alkaline batteries, in black polished brass, zinc objects, ceramics, electrical equipment, enamel (green: nickel oxide), fuel additives, insecticides, reagents and catalysts for plastic material, nickel alloys and coating, magnetic cores, fat hardeners as catalyst and in plating composition for galvanic bath or brass. The nickel is present in several cosmetics in the form of impurities.

The ADC produces cutaneous injuries very similar to those occurring in eczema, in its acute and chronic form. The main symptoms comprises boils formed on skin surface, which appears reddened, itchy, swollen and covered with blisters. The blisters may break forming crusts. If the contact with nickel persists over time, the skin thickens and skin exfoliates by chapping, thereby getting a darker color. In the chronic variant, hyperkeratosis, xerosis and fissures may manifest.

The first symptoms of the allergic contact dermatitis are presence of rash, presence of lesions at the site of exposure. Further the rash is oozed, drained or crust depending on the type of allergen caused. The rash later become raw, scaled and thickened. It is possible that the skin lesion does not take the form of a rash but it includes papules, blisters, vesicles or even a simple red area. In the allergic contact dermatitis, the rash is confined to the area where the trigger or the allergen touches the skin. The rash appears in a day or two after exposure to the allergen. The other symptom includes an itching of skin, skin redness or inflammation, localized swelling and increased temperature in and around rash.

The allergic contact dermatitis is mitigated by avoiding the allergen or the causative agent. The allergen is avoided by evaluation and detection of the itching allergen.

The contact dermatitis symptoms is reduced by the application of creams based on corticosteroids or by orally administering corticosteroids. However, these treatments are given only for a short span of time, as they trigger side effects, even severe side effects.

Therefore, the unique method currently followed to prevent the onset of nickel allergies is to absolutely avoid the contact with nickel-containing products.

Hence there is a need for composition for application on the articles comprising metals causing ADC, for preventing the symptoms of allergic contact dermatitis. Also there is a need for a clear aerosol composition for the application on the surface of metal articles to prevent the symptoms of allergic contact dermatitis in sensitized subjects. Further there is a need for an aerosol composition for avoiding a tarnishing of metal surfaces.

The above mentioned shortcomings, disadvantages and problems are addressed herein and which will be understood by reading and studying the following specification.

OBJECTIVES OF THE EMBODIMENTS

The primary objective of the embodiment herein is to provide a hypoallergic and metal surface sealant composition to prevent skin allergies.

Another object of the embodiment herein is to provide an aerosol composition for coating metal surfaces for protecting the users against skin irritation and to avoid tarnishing of the metal surface.

Yet another object of the embodiment herein is to provide a composition which is sprayed on the surface of metal articles such as jewelry to seal the surface and protect against tarnish and skin irritation.

Yet another object of the embodiment herein is to provide a composition which is easily sprayed on the metal articles for protection against allergies and to avoid corrosion of metal articles.

Yet another object of the embodiment herein is to provide a composition for spraying on metal articles which is self-leveling.

Yet another object of the embodiment herein is to provide a composition for spraying on metal articles which is fast drying and reduces the time of application.

Yet another object of the embodiments herein is to provide a composition for spraying on metal or alloy articles manufactured from the base metals selected from a group consisting of nickel, zinc, lead, tin, copper and aluminum to avoid the allergic reaction and to avoid the corrosion of metal or alloy.

Yet another object of the embodiments herein is to provide a composition for spraying on metal or alloy articles to avoid direct skin contact.

Yet another object of the embodiments herein is to provide a clear aerosol composition for hypoallergenic metal surface sealant which is echo-friendly and biodegradable.

Yet another object of the embodiments herein is to provide a clear aerosol composition hypoallergenic metal surface sealant which is non-toxic.

These objects and the other advantages of the embodiments herein will become readily apparent from the following detailed description taken in conjunction with the accompanying drawings.

SUMMARY

The various embodiments herein provide a clear aerosol, hypoallergenic composition to be used on metals (specifically jewelry) to prevent skin allergies and a tarnishing of metal. The composition preserves the jewelry and protects their skin. The hypoallergic and metal surface sealant composition is an aerosol composition which coats metal surface for protecting the users against skin irritation and to avoid tarnishing of the metal surface to prevent skin allergies.

According to one embodiment herein, a method of synthesizing hypoallergenic metal surface sealant clear aerosol composition comprises the following steps. A resin material is added to ethyl acetate slowly under constant agitation. The concentration of the resin material present in the composition is in a predetermined range. The concentration of the ethyl acetate present in the composition is in a predetermined range. The mixture comprising the resin material and the ethyl acetate is agitated till no lumps are present. The butyl acetate, TXIB Plasticizer, Propylene Glycol Monomethyl Ether Acetate (PM) Acetate, Ethyl acetate, a herbal fragrance and a propellant are added to the mixture comprising resin material and ethyl acetate to obtain a composition. The concentration of the butyl acetate present in the composition is in a predetermined range. The TXIB plasticizer is added in the composition in a predetermined amount. The concentration of the propylene glycol monomethyl ether acetate present in the composition is in a predetermined range. The concentration of the ethyl acetate is present in the composition is in a predetermined range. The herbal fragrance is added in the composition in a predetermined amount. The propellent is added in the composition in a predetermined range. The composition is blended at a predetermined speed to uniformly mix the components.

According to one embodiment herein, the resin material is a paraloid-B-48 material. The concentration of resin present in the composition is in a predetermined range of 3.17-3.2 wt %.

According to one embodiment herein, the concentration of the ethyl acetate present in the composition is in a predetermined range of 9.53-18.1 wt %. The ethyl acetate is a solvent.

According to one embodiment herein, the concentration of the butyl acetate present in the composition is in a predetermined range of 2.54-2.6 wt %. The butyl acetate is a solvent.

According to one embodiment herein, the concentration of the propylene glycol monomethyl ether (PM) acetate is in a predetermined range of 5.93-6 wt %. The propylene glycol monomethyl ether (PM) acetate is a solvent.

According to one embodiment herein, the concentration of the ethyl acetate present in the composition is in a predetermined range of 8.47-18.1 wt %. The ethyl acetate is a solvent.

According to one embodiment herein, the herbal fragrance is a Chemia #46210 Lavandin. The predetermined amount of the herbal fragrance is 0.12 wt %.

According to one embodiment herein, the propellant is a dimethyl ether. The predetermined amount of dimethyl ether is 70 wt %.

According to one embodiment herein, a clear aerosol composition of hypoallergenic metal surface sealant comprises a resin material, an ethyl acetate, a butyl acetate, a TXIB Plasticizer, a Propylene Glycol Monomethyl Ether (PM) Acetate, an ethyl acetate, a herbal fragrance and a propellent. The concentration of the resin material present in the composition is in a predetermined range. The concentration of the ethyl acetate present in the composition is in a predetermined range. The concentration of the butyl acetate present in the composition is in a predetermined range. The TXIB plasticizer is present in the composition in a predetermined amount. The concentration of the propylene glycol monomethyl ether acetate present in the composition is in a predetermined range. The concentration of the ethyl acetate is present in the composition is in a predetermined range. The herbal fragrance is present in the composition in a predetermined amount. The propellent is present in the composition in a predetermined range.

According to one embodiment herein, the resin material is a paraloid-B-48 material. The concentration of resin present in the composition is in the predetermined range of 3.17-3.2 wt %.

According to one embodiment herein, the concentration of the ethyl acetate present in the composition is in the predetermined range of 9.53-18.1 wt %. The ethyl acetate is a solvent.

According to one embodiment herein, the concentration of the butyl acetate present in the composition is in the predetermined range of 2.54-2.6 wt %. The butyl acetate is a solvent.

According to one embodiment herein, the concentration of the propylene glycol monomethyl ether (PM) acetate is present in the predetermined range of 5.93-6 wt %. The propylene glycol monomethyl ether (PM) acetate is a solvent.

According to one embodiment herein, the concentration of the ethyl acetate is in the predetermined range of 8.47-18.1 wt %. The ethyl acetate is a solvent.

According to one embodiment herein, the herbal fragrance is a Chemia #46210 Lavandin. The predetermined amount of the herbal fragrance is 0.12 wt %.

According to one embodiment herein, the propellant is a dimethyl ether. The predetermined amount of dimethyl ether is 70 wt %.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without deportioning from the spirit thereof, and the embodiments herein include all such modifications.

BRIEF DESCRIPTION OF THE DRAWINGS

The other objects, features and advantages will occur to those skilled in the art from the following description of the preferred embodiment and the accompanying drawings in which:

FIG. 1 illustrates a flow chart explaining a method of synthesizing a clear aerosol hypoallergenic metal surface sealant composition, according to one embodiment herein.

Although the specific features of the embodiments herein are shown in some drawings and not in others. This is done for convenience only as each feature may be combined with any or all of the other features in accordance with the embodiments herein.

DETAILED DESCRIPTION OF THE EMBODIMENTS

In the following detailed description, a reference is made to the accompanying drawings that form a portion hereof, and in which the specific embodiments that may be practiced is shown by way of illustration. The embodiments are described in sufficient detail to enable those skilled in the art to practice the embodiments and it is to be understood that the logical, mechanical and other changes may be made without departing from the scope of the embodiments. The following detailed description is therefore not to be taken in a limiting sense.

The various embodiments herein provide hypoallergenic, metal surface sealant clear aerosol composition to be used on metals (specifically jewelry) to prevent skin allergies and the process of tarnishing of metal. The composition preserves the jewelry and protects their skin. The hypoallergic and metal surface sealant composition is an aerosol composition which coats metal surface for protecting the users against skin irritation and to avoid tarnishing of the metal surface to prevent skin allergies.

According to one embodiment herein, a method of synthesizing hypoallergenic metal surface sealant clear aerosol composition comprises the following steps. A resin material is added to ethyl acetate slowly under constant agitation. The concentration of the resin material present in the composition is in a predetermined range. The concentration of the ethyl acetate present in the composition is in a predetermined range. The mixture comprising the resin material and the ethyl acetate is agitated till no lumps are present. The butyl acetate, TXIB Plasticizer, Propylene Glycol Monomethyl Ether Acetate (PM) Acetate, Ethyl acetate, a herbal fragrance and a propellent are added to the mixture comprising resin material and ethyl acetate to obtain a composition. The concentration of the butyl acetate present in the composition is in a predetermined range. The TXIB plasticizer is added in the composition in a predetermined amount. The concentration of the propylene glycol monomethyl ether acetate present in the composition is in a predetermined range. The concentration of the ethyl acetate is present in the composition is in a predetermined range. The herbal fragrance is added in the composition in a predetermined amount. The propellent is added in the composition in a predetermined range. The composition is blended at a predetermined speed to uniformly mix the components.

According to one embodiment herein, the resin material is a paraloid-B-48 material. The concentration of resin present in the composition is in a predetermined range of 3.17-3.2 wt %.

According to one embodiment herein, the concentration of the ethyl acetate present in the composition is in a predetermined range of 9.53-18.1 wt %. The ethyl acetate is a solvent.

According to one embodiment herein, the concentration of the butyl acetate present in the composition is in a predetermined range of 2.54-2.6 wt %. The butyl acetate is a solvent.

According to one embodiment herein, the concentration of the propylene glycol monomethyl ether (PM) acetate is in a predetermined range of 5.93-6 wt %. The propylene glycol monomethyl ether (PM) acetate is a solvent.

According to one embodiment herein, the concentration of the ethyl acetate present in the composition is in a predetermined range of 8.47-18.1 wt %. The ethyl acetate is a solvent.

According to one embodiment herein, the herbal fragrance is a Chemia #46210 Lavandin. The predetermined amount of the herbal fragrance is 0.12 wt %.

According to one embodiment herein, the propellant is a dimethyl ether. The predetermined amount of dimethyl ether is 70 wt %.

According to one embodiment herein, a clear aerosol composition of hypoallergenic metal surface sealant comprises a resin material, an ethyl acetate, a butyl acetate, a TXIB Plasticizer, a Propylene Glycol Monomethyl Ether (PM) Acetate, an ethyl acetate, a herbal fragrance and a propellent. The concentration of the resin material present in the composition is in a predetermined range. The concentration of the ethyl acetate present in the composition is in a predetermined range. The concentration of the butyl acetate present in the composition is in a predetermined range. The TXIB plasticizer is present in the composition in a predetermined amount. The concentration of the propylene glycol monomethyl ether acetate present in the composition is in a predetermined range. The concentration of the ethyl acetate is present in the composition is in a predetermined range. The herbal fragrance is present in the composition in a predetermined amount. The propellent is present in the composition in a predetermined range.

According to one embodiment herein, the resin material is a paraloid-B-48 material. The concentration of resin present in the composition is in the predetermined range of 3.17-3.2 wt %.

According to one embodiment herein, the concentration of the ethyl acetate present in the composition is in the predetermined range of 9.53-18.1 wt %. The ethyl acetate is a solvent.

According to one embodiment herein, the concentration of the butyl acetate present in the composition is in the predetermined range of 2.54-2.6 wt %. The butyl acetate is a solvent.

According to one embodiment herein, the concentration of the propylene glycol monomethyl ether (PM) acetate is present in the predetermined range of 5.93-6 wt %. The propylene glycol monomethyl ether (PM) acetate is a solvent.

According to one embodiment herein, the concentration of the ethyl acetate is in the predetermined range of 8.47-18.1 wt %. The ethyl acetate is a solvent.

According to one embodiment herein, the herbal fragrance is a Chemia #46210 Lavandin. The predetermined amount of the herbal fragrance is 0.12 wt %.

According to one embodiment herein, the propellant is a dimethyl ether. The predetermined amount of dimethyl ether is 70 wt %.

FIG. 1 illustrates a flow chart expalining a method of synthesizing hypoallergenic metal surface sealant clear aerosol composition, according to one embodiment herein. The method of synthesizing clear aerosol hypoallergenic metal surface sealant composition comprises the following steps. The paraloid-B-48 material (10.59 wt %) is added to ethyl acetate (31.77 wt %) slowly under constant agitation (101). The mixture comprising paraloid-B-48 material and ethyl acetate is agitated till no lumps are present (102). The butyl acetate (8.47 wt %), TAXIB Plasticizer (0.70 wt %), propylene glycol monomethyl ether (PM) acetate (19.77 wt %), ethyl acetate (28.24 wt %), Chemia #46210 Lavandin (0.42 wt %) and dimethyl ether to the mixture comprising paraloid-B-48 material and ethyl acetate are added to the mixture comprising paraloid B-48 material and ethyl acetate to obtain a composition (103). The composition is blended at a predetermined speed to uniformly mix the components (104).

Table 1 given below lists the amount of the components present in the hypoallergenic metal surface sealant clear aerosol composition:

| Material | % of formula By Weight | % of the clear By Weight |
|---|---|---|
| Paraloid B-48 | 3.17-3.2 | 10.59 |
| Ethyl Acetate | 9.53-18.1 | 31.77 |
| Butyl Acetate | 2.54-2.6 | 8.47 |
| TXIB Plasticizer | 0.21 | 0.70 |
| PM Acetate | 5.93-6 | 19.77 |
| Ethyl Acetate | 8.47-18.1 | 28.24 |
| Chemia #46210 Lavandin | 0.12 | 0.42 |
| Sub Total | 30.00 | 100.00 |
| DME Propellant | 70.00 | |

Table 2 given below illustrates the role of each of the components present in the hypoallergenic metal surface sealant clear aerosol composition:

| | |
|---|---|
| ACRYLIC RESIN | Protectorant |
| BUTYL ACETATE | Solvent |
| DI-ISOBUTYRATE | Plasticizer |
| DIMETHYL ETHER | Propellant |
| ETHYL ACETATE | Solvent |
| PM ACETATE | Solvent |
| TRIMETHYL PENTANYL | Plasticizer |

According to one embodiment herein, many people have reported an allergy to nickel. Nickel is the most common metal used in most of the artificial jewelry articles. The hypo allergic and metal surface sealant composition is suitable for all metals and alloy's, including nickel. After the application of the hypoallergic and metal surface sealant composition, there is no negative effects or allergies on human skin. Even after bathing, exercising, sleeping, sweating and/or working, the hypo allergic and metal surface sealant composition lasts on the surface of the metal articles and remain of the surface of metal articles for a long duration of time.

According to one embodiment herein, the hypoallergenic metal surface sealant clear aerosol composition sprayed on metal or alloy articles manufactured from the base metals selected from a group consisting of nickel, zinc, lead, tin, copper and aluminum to avoid the allergic reaction and to avoid the corrosion of metal or alloy. The hypoallergenic metal surface sealant clear aerosol composition is sprayed on metal or alloy articles to avoid direct skin contact.

According to one embodiment herein, the hypo allergic and metal surface sealant composition provides long-lasting allergy protection directly to end-users. The composition is easy to apply, as the composition is an aerosol spray to cover the metal or alloy article surface evenly. The hypo allergic and metal surface sealant composition is easily stored in a temperature up to 120° F. The composition dries fast after application. The composition has a mild fruity odor with a lavender undertone. The hypo allergic and metal surface sealant composition protects the user of jewelry from tarnish and skin irritations through a clear and long lasting aerosol coating.

According to one embodiment herein, the efficacy test of the hypo allergic and metal surface sealant composition was performed on thirty participants who are highly susceptible to mild and severe allergic reaction to nickel. A common allergic reaction comprises skin discoloration, redness, rashes and hives. Each participant wore a jewelry article that is sprayed with the hypo allergic and metal surface sealant composition for a nonstop duration of thirty days, even while sleeping, bathing, working and etc. Throughout the test period, the jewelry coated with the hypoallergic and metal surface sealant composition is tested against elements/factors that provoke tarnishing and skin reactions. The elements/factors affecting the hypo allergic and metal surface sealant composition include water, humidity, sweat, skin oils/acids and cosmetic products. It is observed that twenty-seven of the thirty participants reported no sign of tarnish or skin discoloration. Only three participants showed slight jewelry discoloration near the end of the efficacy test, in which the hypo allergic and metal surface sealant composition significantly delayed that process.

According to one embodiment herein, the hypo allergenic, clear aerosol composition is applied on necklaces, bracelets, rings, earrings, body jewelry, chains, belts, glasses, brooches, watches, buttons, screws and fasteners (threaded fasteners where protection is needed against rusting and oxidation). The hypoallergic and metal surface sealant composition can also be formulated in liquid form for plating on the metal or alloy articles. The hypo allergic and metal surface sealant composition is not just limited to an aerosol propellant/gas mixture.

According to one embodiment herein, the manufacturers suffer great loss during a fabricating or manufacturing of the metal goods that are prone to tarnish, corrosion and cause allergic reaction when the goods come in direct contact with human skin. The industrial products that are susceptible to a tarnishing through an exposure to oxidation, moisture, and humidity. The industrial-metal products, such as industrial screws, fasteners and other hardware tarnish, corrode and rust. The tarnish, corrosion and rust make the industrial metal products ineffective and hazardous for commercial use. The following industries mass produce metal products, in which they experience regular tarnishing and the risk of their customers suffering a skin allergy to their products. The industries are automotive, agricultural equipment, military/government equipment, aerospace, technology, home appliance, medical equipment and marine equipment.

According to one embodiment herein, the hypoallergenic, clear aerosol composition the Tarnish-Me-Not provides immense value towards industrial manufacturers within the industries listed above. During production, these manufacturers are prompted to dip the metal products into the liquid formula of hypoallergenic, clear aerosol composition, which dries to a plating that preserves the metals from tarnishing and eliminates the risk of consumers having exposure to the base metals that cause allergies and irritation.

The foregoing description of the specific embodiments will so fully reveal the general nature of the embodiments herein that others can, by applying current knowledge, readily modify and/or adapt for various applications such specific embodiments without deportioning from the generic concept, and, therefore, such adaptations and modifications should and are intended to be comprehended within the meaning and range of equivalents of the disclosed embodiments.

It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

Although the embodiments herein are described with various specific embodiments, it will be obvious for a person skilled in the art to practice the invention with modifications. However, all such modifications are deemed to be within the scope of the claims.

It is also to be understood that the following claims are intended to cover all of the generic and specific features of the embodiments described herein and all the statements of the scope of the embodiments which as a matter of language might be said to fall there between.

What is claimed is:

1. A clear aerosol composition for hypoallergic metal surface sealant, the composition comprises:
    a resin material, and wherein a concentration of the resin material present in the composition is in a predetermined range;
    an ethyl acetate, and wherein a concentration of the ethyl acetate present in the composition is in a predetermined range;
    an butyl acetate, and wherein a concentration of the butyl acetate present in the composition is in a predetermined range;
    a Plasticizer comprising trimethyl pentanyl diisobutyrate, and wherein the plasticizer comprising trimethyl pentanyl diisobutyrate is added in the composition in a predetermined amount;
    a Propylene Glycol Monomethyl Ether Acetate (PM) Acetate, a concentration of the propylene glycol monomethyl ether acetate present in the composition is in a predetermined range;
    a herbal fragrance, and wherein the herbal fragrance is added in the composition in a predetermined amount; and
    a propellent, and wherein the propellant is added in the composition in a predetermined range.

2. The composition according to claim 1, wherein the resin material is an acrylic resin material, and wherein the concentration of the resin material present in the composition is in the predetermined range of 3.17-3.2 wt %.

3. The composition according to claim 1, wherein the concentration of the ethyl acetate present in the composition is in the predetermined range of 9.53-18.1 wt %, and wherein the ethyl acetate is a solvent.

4. The composition according to claim 1, wherein the concentration of the butyl acetate present in the composition is in the predetermined range of 2.54-2.6 wt % and wherein the butyl acetate is a solvent.

5. The composition according to claim 1, wherein the concentration of the propylene glycol monomethyl ether (PM) acetate is in the predetermined range of 5.93-6 wt %, and wherein the propylene glycol monomethyl ether (PM) acetate is a solvent.

6. The composition according to claim 1, wherein the concentration of the ethyl acetate is in the predetermined range of 8.47-18.1 wt %, and wherein the ethyl acetate is a solvent.

7. The composition according to claim 1, wherein the predetermined amount of the herbal fragrance is 0.12 wt %.

8. The composition according to claim 1, wherein the propellant is a dimethyl ether, and wherein the predetermined amount of dimethyl ether is 70 wt %.

* * * * *